United States Patent [19]

Devlin et al.

[11] 3,998,962
[45] Dec. 21, 1976

[54] PHARMACEUTICAL COMPOSITIONS CONTAINING A 2-CARBOXY-4-OXO-4H, 10H-(2)-BENZOPYRANO-[4,3-G]-(1) BENZOPYRAN OR A SALT THEREOF AND METHOD OF USE

[75] Inventors: John Devlin, Pierrefonds; Patrick Brian Stewart, St. Andrews East; Kurt Freter, Beaconsfield, all of Canada

[73] Assignee: Boehringer Ingelheim GmbH, Ingelheim am Rhein, Germany

[22] Filed: June 16, 1975

[21] Appl. No.: 587,331

Related U.S. Application Data

[63] Continuation-in-part of Ser. No. 392,182, Aug. 28, 1973, Pat. No. 3,901,925.

[30] Foreign Application Priority Data

Aug. 29, 1972 Austria .................... 7425/72

[52] U.S. Cl. .................................. 424/283
[51] Int. Cl.² ............................... A61K 31/35
[58] Field of Search ............. 424/283, 279

[56] References Cited
UNITED STATES PATENTS

| | | | |
|---|---|---|---|
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

OTHER PUBLICATIONS

Physician's Desk Reference, (PDR), (1974), pp. 760–761 referring to "Intal".

*Primary Examiner*—Norman A. Drezin
*Attorney, Agent, or Firm*—Hammond & Littell

[57] ABSTRACT

Pharmaceutical dosage unit compositions containing as an active ingredient a compound of the formula

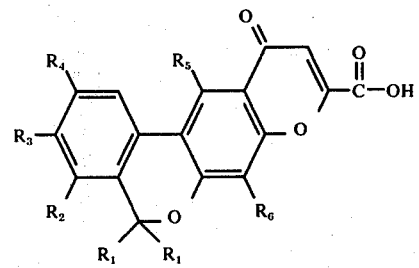

wherein $R_1$ is hydrogen or lower alkyl,
 $R_2$, $R_4$ and $R_5$, which may be identical to or different from each other, are each hydrogen, lower alkyl, hydroxyl, lower alkoxy, acyloxy, halogen, nitro or —$SO_3H$, and
 $R_3$ and $R_6$, which may be identical to or different from each other, are each hydrogen, lower alkyl, hydroxyl, lower alkoxy, acyloxy, halogen, nitro, —$SO_3H$, hydroxycarbonyl-methoxy, β-hydroxyethoxy or β-amino-ethoxy, or a salt thereof; and a method of using the same as antiallergics.

10 Claims, No Drawings

PHARMACEUTICAL COMPOSITIONS CONTAINING A 2-CARBOXY-4-OSO-4H,10H-(2)-BENZOPYRANO-[4,3-G]-(1) BENLOPYRAN OR A SALT THEREOF AND METHOD OF USE

This is a continuation-in-part of copending application Ser. No. 392,182 filed Aug. 28, 1973, now U.S. Pat. No. 3,901,925, granted Aug. 26, 1975.

This invention relates to novel pharmaceutical dosage unit compositions containing a 2-carboxy-4-oxo-4H,10H-(2)-benzopyrano-[4,3-g]-benzopyran or a salt thereof, as well as to a method of using the same as antiallergics.

More particularly, the present invention relates to antiallergic pharmaceutical dosage unit compositions consisting essentially of an inert pharmaceutical carrier and an effective antiallergic amount of a benzopyrano-benzopyran of the formula

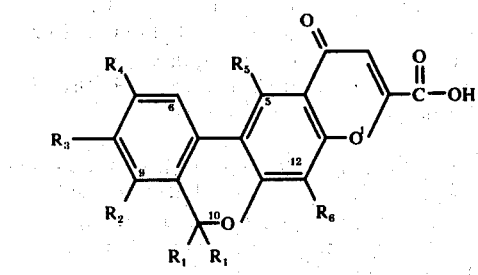

(I)

wherein $R_1$ is hydrogen or lower alkyl, $R_2$, $R_4$ and $R_5$, which may be identical to or different from each other, are each hydrogen, lower alkyl, hydroxyl, lower alkoxy, acyloxy, halogen, nitro or $-SO_3H$, and $R_3$ and $R_6$, which may be identical to or different from each other, are each hydrogen, lower alkyl, hydroxyl, lower alkoxy, acyloxy, halogen, nitro, $-SO_3H$, hydroxycarbonyl-methoxy, $\beta$-hydroxy-ethoxy or $\beta$-amino-ethoxy, and salts thereof.

The compounds embraced by formula I may be prepared by the following methods:

Method A

By reacting a 2-acetyl-3-hydroxy-6H-dibenzo[b,d]-pyran of the formula

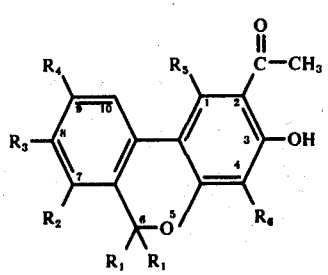

(II)

wherein $R_1$ through $R_6$ have the same meanings as in formula I, with an oxalic acid ester, especially a di-lower alkyl oxalate.

The reaction is preferably carried out in a basic, non-aqueous medium, such as sodium alcoholate. The reactants are advantageously first dissolved or suspended in a non-aqueous solvent, such as ethanol, and the solution or suspension is introduced into the basic medium at room temperature or while gently warming. The reaction mixture is then refluxed for some time, and, after cooling, the raw condensation product is refluxed in acetic acid, preferably in the presence of an aqueous mineral acid, such as concentrated hydrochloric acid.

Method B

By treating a 6H-dibenzo[b,d]pyranyl-(3)-fumaric acid ether of the formula

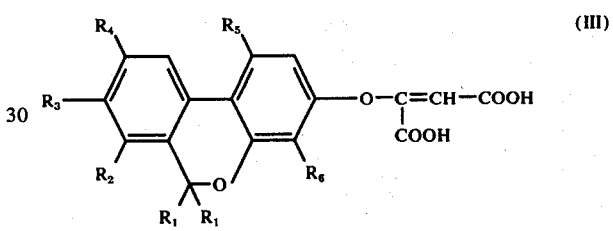

(III)

wherein $R_1$ through $R_6$ have the same meanings as in formula I, with a strong mineral acid, preferably sulfuric acid. The dibenzopyranyl-fumaric acid ether is dissolved in the mineral acid, the solution is allowed to stand at room temperature, and the reaction mixture is worked up in conventional manner.

The free acid obtained as the desired end product in methods A and B may, if desired, be converted into a salt thereof with a base, such as the sodium salt. For this purpose the free acid is dissolved or suspended in water, and then the desired base is added to the solution or suspension until it has a pH of 7. The resulting solution of the salt is then preferably freeze-dried, because of the possibility that the salt may decompose if the solution thereof is evaporated.

The starting compounds of the formula II for method A are accessible, for example, by a. the Fries rearrangement [K. Fries et al, Berichte 41, 4271 (1908); and, ibid. 43, 212 (1910)] of the acetic acid ester (V) of a phenol (IV) in the presence of aluminum chloride; or b. direct acetylation of a phenol (IV) with acetic acid/boron trifluoride, pursuant to the following schematic reaction sequences:

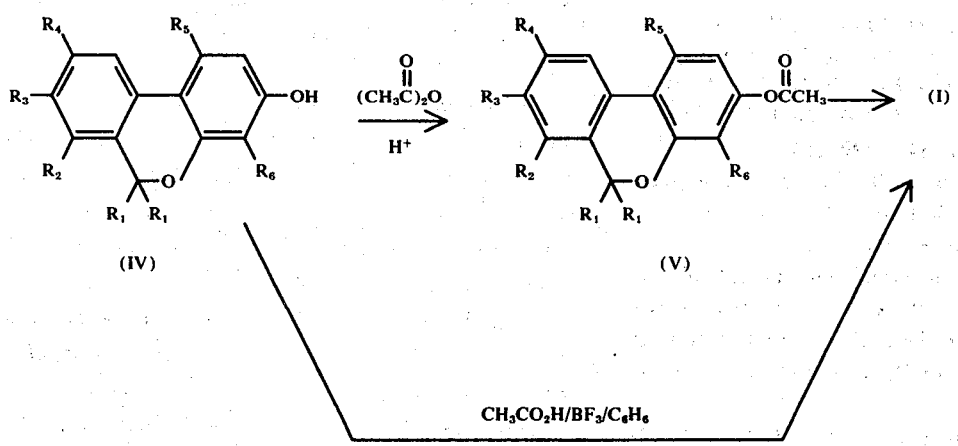

A phenol of the formula IV in turn is obtained, when $R_1$ is to be hydrogen, by reduction with diborane-borontrifluoride or, when $R_1$ is to be lower alkyl, by Grignard alkylation of a corresponding lactone of the formula

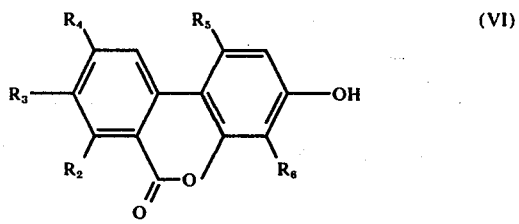

where $R_2$ through $R_6$ have the meanings previously defined.

A lactone of the formula VI may be prepared from a correspondingly substituted o-bromo-benzoic acid with the aid of a suitable resorcinol derivative pursuant to the method of W. R. H. Hurtley, J. Chem. Soc. 1929, page 1870.

A fumaric acid pyranyl ether of the formula III may, for example, be prepared by reacting a phenol of the formula IV with dimethylacetylene-dicarboxylic acid in a basic medium.

By means of the above methods and procedures the following 2-carboxy-4-oxo-benzopyranobenzopyrans or their salts may be prepared:

2-carboxy-4-oxo-4H,10H-(2)-benzopyrano-[4,3-g]-(1)-benzopyran,
2-carboxy-4-oxo-10,10-dimethyl-4H,10H-(2)-benzopyrano-[4,3-g]-(1)-benzopyran,
2-carboxy-4-oxo-8-fluoro-10,10-dimethyl-4H,10H-(2)-benzopyrano-[4,3-g]-(1)-benzopyran,
2-carboxy-4-oxo-8-chloro-10,10-dimethyl-4H,10H-(2)-benzopyrano-[4,3-g]-(1)-benzopyran,
2-carboxy-4-oxo-9-chloro-10,10-dimethyl-4H,10H-(2)-benzopyrano-[4,3-g]-(1)-benzopyran,
2-carboxy-4-oxo-8-methoxy-10,10-dimethyl-4H,10H-(2)-benzopyrano-[4,3-g]-(1)-benzopyran,
2-carboxy-4-oxo-7,8-dimethoxy-10,10-dimethyl-4H,10H-(2)-benzopyrano-[4,3-g]-(1)-benzopyran,
2-carboxy-4-oxo-7,9-dimethoxy-10,10-dimethyl-4H,10H-(2)-benzopyrano-[4,3-g]-(1)-benzopyran,
2-carboxy-4-oxo-10,10-di-n-butyl-4H,10H-(2)-benzopyrano-[4,3-g]-(1)-benzopyran,
2-carboxy-4-oxo-7-bromo-8-methoxy-10,10-dimethyl-4H,10H-(2)-benzopyrano-[4,3-g]-(1)-benzopyran,
2-carboxy-4-oxo-5,10,10-trimethyl-4H,10H-(2)-benzopyrano-[4,3-g]-(1)-benzopyran,
2-carboxy-4-oxo-8-nitro-10,10-dimethyl-4H,10H-(2)-benzopyrano-[4,3-g]-benzopyran, and
2-carboxy-4-oxo-8-sulfo-10,10-dimethyl-4H,10H-(2)-benzopyrano-[4,3-g]-(1)-benzopyran.

The following examples further illustrate the present invention and will enable others skilled in the art to understand it more completely. It should be understood, however, that the invention is not limited solely to the particular examples given below.

EXAMPLE 1

2-Carboxy-4-oxo-4H,10H-(2)-benzopyrano-[4,3-g]-(1)-benzopyran by method A

A suspension of 3.8 gm (0.016 mol) of 2-acetyl-3-hydroxy-6H-dibenzo[b,d]pyran (m.p. 128°–130° C) in a mixture consisting of 4.3 gm (0.029 mol) of diethyl oxalate and 60 ml of ethanol was stirred all at once into a solution of 3.3 gm (0.145 mol) of sodium in 60 ml of ethanol at 55° C, and the resulting mixture was refluxed for 90 minutes. Thereafter, the reaction mixture was cooled to 15° C, and the solid raw condensation product was filtered, dried and refluxed for 30 minutes in a mixture of 53 ml of acetic acid and 20 ml of concentrated hydrochloric acid. Subsequently, the reaction mixture was cooled and then filtered, and the filter cake was purified by dissolving it in a saturated aqueous sodium bicarbonate solution, re-precipitating it therefrom with 2N hydrochloric acid, and recrystallizing it twice from aqueous dimethylsulfoxide. 2.6 gm (56% of theory) of the compound of the formula

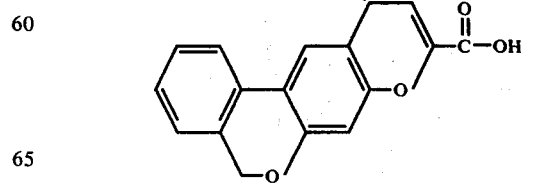

with a melting point of 309°–311° C were obtained.

EXAMPLE 2

2-Carboxy-4-oxo-10,10-dimethyl-4H,10H-(2)-benzopyrano-[4,3-g]-(1)-benzopyran by method B A mixture consisting of 2.2 gm (0.01 mol) of 3-hydroxy-6,6-dimethyl-6H-dibenzo[b,d]pyran and 1.4 gm (0.01 mol) of dimethyl acetylene-dicarboxylate was heated on a steam bath, and four drops of benzyl trimethylammonium hydroxide were added thereto. The reddish-brown oil formed thereby was heated on the steam bath for 20 minutes more, and was then admixed with a solution of 1.1 gm (0.027 mol) of sodium hydroxide in 6 ml of water and 3.2 ml of methanol. The resulting mixture was heated for 40 minutes at 80° C, then diluted with 100 ml of water, adjusted to pH 7.5 with 2N phosphoric acid and extracted twice with 50 ml of ether each. The aqueous phase was acidified to pH 4 and was then extracted four times with 50 ml of ether each. The combined ethereal extracts contained the desired 6,6-dimethyl-6H-dibenzo[b,d]pyranyl-(3)-fumaric acid ether, which was precipitated as and purified in conventional manner by way of its diethanolamine salt, yielding 2.2 gm (48% of theory) of the salt which had a melting point of 170°–175° C.

1.6 gm of 6,6-dimethyl-6H-dibenzo[b,d]pyranyl-(3)-fumaric acid ether, obtained by acidifying the diethanolamine salt produced in the preceding step, were dissolved in 50 ml of concentrated sulfuric acid, and the solution was allowed to stand at room temperature for 16 hours. Thereafter, the reaction mixture was poured over 300 gm of ice, and the mixture was filtered. The filter cake was dissolved in 2N aqueous sodium carbonate, and the resulting solution was adjusted to pH 8 with 2N phosphoric acid and then extracted with chloroform. The aqueous phase was now brought to pH 4.5 with 2N phosphoric acid and was then extracted three times with 50 ml each of a mixture of chloroform and methanol (9:1). The combined extracts were dried, the solvent was evaporated, and the residue was recrystallized from aqueous dimethylsulfoxide, yielding 748 mgm (51% of theory) of the compound of the formula

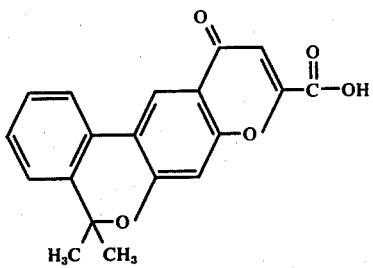

which had a melting point of 247°–250° C (decomp.).

EXAMPLE 3

2-Carboxy-4-oxo-10,10-di-n-butyl-4H,10H-(2)-benzopyrano-[4,3-g]-(1)-benzopyran by method A A solution of 5.5 gm (0.016 mol) of 2-acetyl-3-hydroxy-6,6-di-n-butyl-6H-dibenzo[b,d]pyran (an oil) and 4.2 gm (0.028 mol) of diethyl oxalate in 50 ml of ethanol was stirred all at once into a solution of 3.2 gm (0.14 mol) of sodium in 75 ml of ethanol at 43° C, and the resulting mixture was refluxed for 30 minutes and then cooled to 5° C. The solid reaction product formed thereby was isolated, dried, admixed with 43 ml of acetic acid and 17.5 ml of concentrated hydrochloric acid, and the mixture was refluxed for 50 minutes. Thereafter, the reaction mixture was allowed to cool, and the raw reaction product was collected and recrystallized twice from aqueous dimethylsulfoxide, yielding 2.2 gm (35% of theory) of 2-carboxy-4-oxo-10,10-di-n-butyl-4H,10H-(2)-benzopyrano-[4,3-g]-(1)-benzopyran having a melting point of 230°–232° C (sintering beginning at 225° C).

EXAMPLE 4

2-Carboxy-4-oxo-8-methoxy-10,10-dimethyl-4H,10H-(2)-benzopyrano-[4,3-g]-(1)-benzopyran by method A A solution of 300 mgm (0.001 mol) of 2-acetyl-3-hydroxy-6,6-dimethyl-8-methoxy-6H-dibenzo[b,d]pyran (an oil) and 0.27 gm (0.018 mol) of diethyl oxalate in 4 ml of ethanol was added all at once to a stirred solution of 0.21 gm (0.009 mol) of sodium in 6 ml of ethanol at 50° C, and the resulting mixture was refluxed for 30 minutes and then cooled to 10° C. The raw condensation product was collected, dried, admixed with 2.3 ml of acetic acid and 0.83 ml of concentrated hydrochloric acid, and the mixture was refluxed for 75 minutes. Thereafter, the reaction mixture was cooled, and the insoluble yellow crystals formed thereby were collected by filtration and recrystallized from methanol, yielding 170 mgm (48% of theory) of the compound of the formula

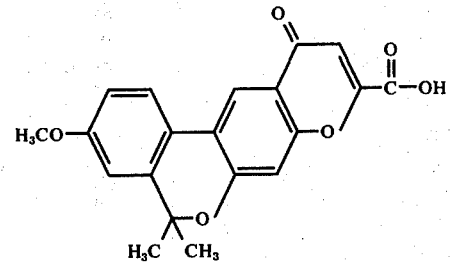

which had a melting point range of 230°–274° C.

| Analysis: | $C_{20}H_{16}O_6$ | |
|---|---|---|
| Calculated: | C — 68.18% ; | H — 4.58% |
| Found: | C — 67.96% ; | H — 4.74% |

EXAMPLE 5

2-Carboxy-4-oxo-8-chloro-10,10-dimethyl-4H,10H-(2)-benzopyrano-[4,3-g]-(1)-benzopyran by method A A suspension of 3.3 gm (0.011 mol) of 2-acetyl-3-hydroxy-6,6-dimethyl-8-chloro-6H-dibenzo[b,d]pyran (m.p. 204°–205° C) in a mixture of 3.0 gm (0.0205 mol) of diethyl oxalate and 45 ml of ethanol was stirred all at once into a solution of 2.3 gm (0.1 mol) of sodium in 55 ml of ethanol at 45° C, and the resulting mixture was refluxed for 20 minutes and then cooled to 8° C. The solid raw condensation product formed thereby was collected, dried, admixed with 32 ml of acetic acid and 11.5 ml of concentrated hydrochloric acid, and the mixture was refluxed for 45 minutes. Thereafter, the reaction mixture was cooled to 25° C, filtered, and the filter cake was recrystallized from aqueous dimethylsulfoxide, yielding 2.1 gm (54% of theory) of the compound of the formula

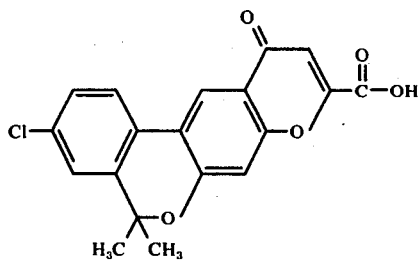

which had a melting point of 304°–306° C.

EXAMPLE 6

2-Carboxy-4-oxo-9-chloro-10,10-dimethyl-4H,10H-(2)-benzopyrano-[4,3-g]-(1)-benzopyran by method A A suspension of 730 mgm (0.024 mol) of 2-acetyl-3-hydroxy-6,6-dimethyl-9-chloro-6H-dibenzo[b,d]pyran (m.p. 172°–175° C) in a mixture consisting of 670 mgm (0.0046 mol) of diethyl oxalate and 8 ml of ethanol was stirred all at once into a solution of 550 mgm (0.024 mol) of sodium in ethanol at 45° C, and the resulting mixture was refluxed for 20 minutes and then cooled to 10° C. The solid raw condensation product was collected, added to a mixture of 8 ml of acetic acid and 3 ml of concentrated hydrochloric acid, and the resulting mixture was refluxed for 1 hour. Thereafter, the reaction mixture was cooled, and the insoluble light-brown crystals formed thereby were collected and recrystallized from aqueous dimethylsulfoxide, yielding 390 mgm (46% of theory) of 2-carboxy-4-oxo-9-chloro-10,10-dimethyl-4H,10H-(2)-benzopyrano-[4,3-g]-(1)-benzopyran which had a melting point of 290°–292° C.

EXAMPLE 7

2-Carboxy-4-oxo-7,8-dimethoxy-10,10-dimethyl-4H,10H-(2)-benzopyrano-[4,3-g]-(1)-benzopyran by method A A suspension of 270 mgm (0.82 millimols) of 2-acetyl-3-hydroxy-6,6-dimethyl-8,9-dimethoxy-6H-dibenzo[b,d]pyran in a mixture of 8 ml of ethanol and 238 mgm (1.63 millimols) of diethyl oxalate was stirred into a solution of 200 mgm (8.7 millimols) of sodium in 4 ml of ethanol at 40° C, and the resulting mixture was refluxed for 40 minutes and then cooled to 10° C. The raw, insoluble condensation product (400 mgm) was collected, dried, added to a mixture of 2.2 ml of acetic acid and 0.9 ml of concentrated hydrochloric acid, and the mixture was refluxed for 1 hour. Thereafter, the reaction mixture was cooled, and the raw, insoluble reaction product was collected, washed with water, and recrystallized twice from methanol, yielding 180 mgm (58% of theory) of the compound of the formula

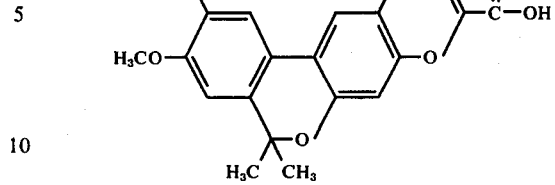

which had a melting point of 294°–295° C.

EXAMPLE 8

2-Carboxy-4-oxo-7-bromo-8-methoxy-10,10-dimethyl-4H,10H-(2)-benzopyrano-[4,3-g]-(1)-benzopyran by method A A suspension of 3.0 gm (0.008 mol) of 2-acetyl-3-hydroxy-6,6-dimethyl-8-methoxy-9-bromo-10H-dibenzo[b,d]pyran in a solution of 2.2 gm (0.015 mol) of diethyl oxalate in ethanol was poured at 75° C into a solution of 1.6 gm (0.07 mol) of sodium in ethanol, and the resulting mixture was refluxed for 45 minutes and then cooled to about 10° C. The solid, raw condensation product was collected, added to a mixture of 17.5 ml of acetic acid and 14 ml of concentrated hydrochloric acid, and the resulting mixture was refluxed for three hours. Thereafter, the reaction mixture was cooled, and the precipitate formed thereby (2.3 gm; 67% of theory) was collected; it was identified to be a mixture of the compound named in the heading and its ethyl ester. This mixture was suspended in 100 ml of water, the suspension was treated for 10 minutes at room temperature with 10 ml of aqueous 10% ethylamine solution, the solution obtained thereby was filtered, the filtrate was acidified with 6N hydrochloric acid, and the precipitate formed thereby was collected and recrystallized from dimethylsulfoxide, yielding 1.4 gm (41% of theory) of the compound of the formula

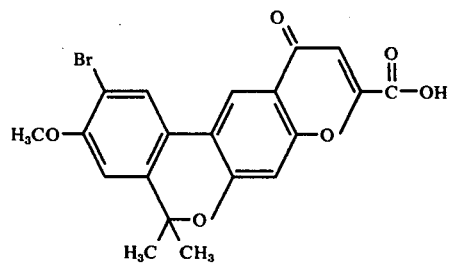

which had a melting point of 312°–318° C.

EXAMPLE 9

2-Carboxy-4-oxo-8-fluoro-10,10-dimethyl-4H,10H-(2)-benzopyrano-[4,3-g]-(1)-benzopyran by method A A suspension of 13.5 gm (0.047 mol) of 2-acetyl-3-hydroxy-6,6-dimethyl-8-fluoro-6H-dibenzo[b,d]pyran in a solution of 12.5 gm (0.0860 mol) of diethyl oxalate in 100 ml of ethanol was stirred all at once into a solution of 9.6 gm (0.41 mol) of sodium in 200 ml of ethanol at 75° C, and the mixture was refluxed for 15 minutes and then cooled to about 10° C. The solid, raw condensation product was collected, dried, added to a mixture of 103 ml of acetic acid and 41 ml of hydrochloric acid, and the resulting mixture was refluxed for 30 minutes. Thereafter, the reaction mixture was cooled, and the solid, raw reaction product (8.0 gm) precipitated thereby was collected and washed with water; an additional 2.0 gm of the raw product were obtained upon letting the mother liquor stand for some time. The combined batches of raw product (10 gm) were stirred for 5 minutes at room temperature with a solution of 1.8 gm (0.03 mol) of ethanolamine in 100 ml of water, the insoluble matter was filtered off, the filtrate was acidified with hydrochloric acid, and the precipitate formed thereby was collected, washed, dried and recrystallized from methanol, yielding 6.2 gm (62.5% of theory) of 2-carboxy-4-oxo-8-fluoro-10,10-dimethyl-4H,10H-(2)-benzopyrano-[4,3-g]-(1)-benzopyran having a melting point of 297°–300° C.

EXAMPLE 10

2-Carboxy-4-oxo-5,10,10-trimethyl-4H,10H-(2)-benzopyrano-[4,3-g]-(1)-benzopyran by method A A solution of 1.41 gm (0.005 mol) of 1,6,6-trimethyl-2-acetyl-3-hydroxy-6H-dibenzo[b,d]pyran and 1.4 gm (0.009 mol) of diethyl oxalate in 20 ml of ethanol was poured into a solution of 1.15 gm (0.05 mol) of sodium in 40 ml of ethanol at 45° C, while stirring, and the resulting mixture was refluxed for three hours and then cooled to 5° C. The precipitate formed thereby was collected, yielding 0.15 gm of the sodium salt of the raw condensation product.

The residual ethanolic solution was acidified with an excess (60 ml) of 2N hydrochloric acid, and the acidic solution was extracted three times with 50 ml each of ether. The combined ethereal extracts were washed three times with 20 ml each of water, dried over sodium sulfate, and the solvent was evaporated, leaving 1.9 gm of the free phenolic form of the raw condensation product.

The sodium salt and the free phenolic form of the raw condensation product were separately refluxed for one hour with a mixture of acetic acid and hydrochloric acid, and each reaction mixture was then cooled to 10° C. The raw, insoluble reaction product from each batch was collected, and the two products were combined and recrystallized three times from ethanol, yielding 1.08 gm (65% of theory) of the compound of the formula

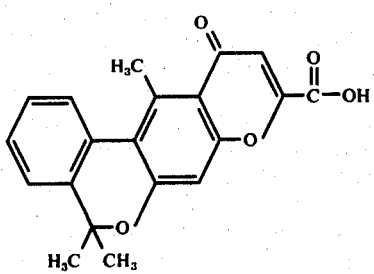

which had a melting point of 281°–285° C.

EXAMPLE 11

2-Carboxy-4-oxo-8-hydroxy-10,10-dimethyl-4H,10H-(2)-benzopyrano-[4,3-g]-(1)-benzopyran by method A A suspension of 5 gm (0.0176 mol) of 2-acetyl-3,8-dihydroxy-10,10-dimethyl-6H-dibenzo[b,d]pyran in a mixture of 30 ml of ethanol and 4.7 gm (0.032 mol) of diethyl oxalate was added to a solution of 4 gm (0.17 mol) of sodium in 70 ml of ethanol at 75° C, and the resulting mixture was refluxed for 40 minutes and then cooled to 12° C. The precipitated raw condensation product was collected, dried and added to a mixture of 38.6 ml of acetic acid and 15.7 ml of concentrated hydrochloric acid, and the resulting mixture was refluxed for 30 minutes. Thereafter, the reaction mixture was cooled, and the precipitate formed thereby was collected, yielding 2.15 gm of a substance which was identified to be a mixture of the compound named in the heading and the ethyl ester thereof. The mixture was treated with 100 ml of aqueous 2N sodium carbonate solution for 10 minutes at room temperature, and then 1.0 gm of the insoluble ester was filtered off, and the filtrate was acidified with 6N hydrochloric acid. The precipitate formed thereby was collected and recrystallized from aqueous dimethylsulfoxide, yielding 1.15 gm (20% of theory) of the compound of the formula

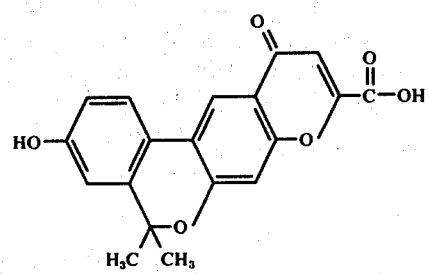

which had a melting point of 305°–308° C.

EXAMPLE 12

2-Carboxy-4-oxo-8-acetoxy-10,10-dimethyl-4H,10H-(2)-benzopyrano-[4,3-g]-(1)-benzopyran A mixture consisting of 500 mgm (0.0015 mol) of 2-carboxy-4-oxo-8-hydroxy-10,10-dimethyl-4H,10H-(2)-benzopyrano-[4,3-g]-(1)-benzopyran (see preceding example) and 1 gm (0.01 mol) of acetic acid anhydride containing 5% sulfuric acid was heated for 10 minutes at 100° C. Thereafter, the reaction mixture was cooled and suspended in 10 ml of ether, and the precipitate formed thereby was collected by filtration, washed with water and recrystallized from ethyl acetate, yielding 340 mgm (65% of theory) of the pale yellow crystalline compound of the formula

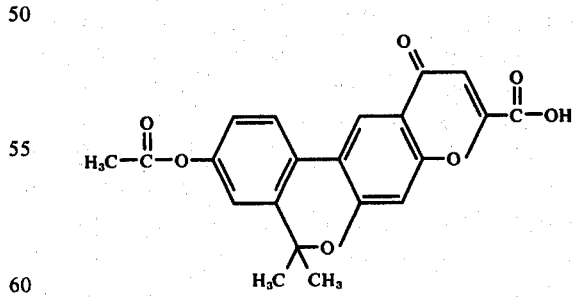

which had a melting point above 340° C (decomp. >260° C) Despite the undefinitive melting point, the end product was found to be analytically and spectroscopically pure.

Analysis: $C_{21}H_{16}O_7$

| Calculated: | C — 66.31% ; | H — 4.24% |
|---|---|---|
| Found: | C — 65.99% ; | H — 4.08% |

EXAMPLE 13

2-Carboxy-4-oxo-8-nitro-10,10-dimethyl-4H,10H-(2)-benzopyrano-[4,3-g]-(1)-benzopyran 20 ml of fuming nitric acid (density 1.60) were added dropwise over a period of one hour to a suspension of 5 gm (0.0155 mol) of 2-carboxy-4-oxo-10,10-dimethyl-4H,10H-(2)-benzopyrano-[4,3-g]-(1)-benzopyran (see Example 2) in 100 ml of glacial acetic acid, while cooling to maintain the temperature of the mixture below 30° C. Thereafter, the temperature of the resulting mixture was allowed to rise to 40° C, and this temperature was maintained for 24 hours. The crystalline yellow precipitate formed thereby was collected, washed with hot ethanol and recrystallized from glacial acetic acid, yielding 2.6 gm (45% of theory) of the compound of the formula

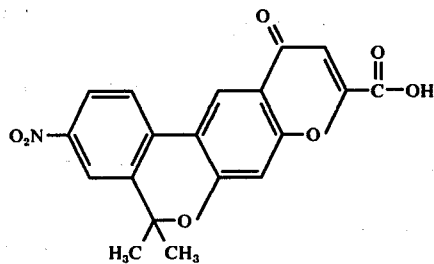

which had a melting point of 293°–300° C.

EXAMPLE 14

2-Carboxy-4-oxo-8-sulfo-10,10-dimethyl-4H,10H-(2)-benzopyrano-[4,3-g]-(1)-benzopyran A solution of 5 gm (0.0155 mol) of 2-carboxy-4-oxo-10,10-dimethyl-4H,10H-(2)-benzopyrano-[4,3-g]-(1)-benzopyran in 92 gm of concentrated sulfuric acid was allowed to stand for five days at room temperature. Thereafter, the reaction mixture was poured over 100 gm of ice, and the resulting aqueous mixture was made alkaline with aqueous 50% sodium hydroxide. The alkaline solution was then adjusted to pH 6 with 2N phosphoric acid, and was then extracted with chloroform-methanol (9:1) to remove unreacted starting material. The aqueous phase was adjusted to pH 1 with 4N hydrochloric acid, and the precipitate formed thereby was collected and recrystallized first from dimethylsulfoxide/acetic acid/ether and then from water, yielding 1.3 gm (21% of theory) of the compound of the formula

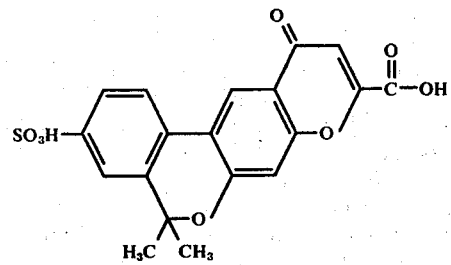

which had a melting point above 350° C (decomp. >290° C)

EXAMPLE 15

2-Carboxy-4-oxo-8-($\beta$-hydroxy-ethoxy)-10,10-dimethyl-4H,10H-(2)-benzopyrano-[4,3-g]-(1)-benzopyran A mixture of 40 gm (0.11 mol) of 2-ethoxycarbonyl-4-oxo-8-hydroxy-10,10-dimethyl-4H,10H-(2)-benzopyrano-[4,3-g]-(1)-benzopyran (see Example 11), 22.8 gm of finely powdered anhydrous potassium carbonate (0.165 mol) and 96.5 gm (1.1 mols) of ethylene carbonate was heated at 110° C for 40 minutes. The reaction mixture was then cooled, diluted with 3 liters of water and filtered. The filtrate was acidified, and the insoluble crude product (41 gm; 96% yield) was collected, dissolved in dimethylformamide containing one equivalent of ethanolamine, and precipitated as the ethanolamine salt by the addition of ether. The crude salt was applied to a silicagel column and chromatographed (butanol/acetic acid/water = 80/10/10). The main fraction upon concentration and acidification yielded the compound named in the heading as a yellow crystalline solid (32 gm; yield 77%). One crystallization from ethanol yielded yellow needles, m.p. 265°–272° C.

EXAMPLE 16

2-Carboxy-4-oxo-12-methoxy-4H,10H-(2)-benzopyrano-[4,3-g]-(1)-benzopuran

A suspension of 370 mgm of 2-acetyl-3-hydroxy-4-methoxy-6H-dibenzo[b,d]pyran (1.4 millimols) in 10 ml of ethanol containing 400 mgm of diethyl oxalate (2.7 millimols) was added all at once to a hot solution of 280 mgm of sodium (12 millimols) in 5 ml of ethanol, and the resulting mixture was refluxed for 45 minutes. The reaction mixture was then cooled, diluted to 100 ml with ice water, and acidified with 2 N hydrochloric acid. The precipitated solid was collected and refluxed in 6 ml of a mixture of acetic acid and hydrochloric acid (2:1) for 30 minutes. Thereafter, the reaction mixture was cooled and poured into ice water. The crude product collected as an insoluble solid and was recrystallized from methanol/tetrahydrofuran to yield the compound named in the heading (310 mgm; 68% yield) as pale yellow needles, m.p. 268°–276° C (decomp.).

EXAMPLE 17

2-Carboxy-4-oxo-12-hydroxy-4H,10H-(2)-benzopyrano-[4,3-g]-(1)-benzopyran

A suspension of 140 mgm of 2-carboxy-4-oxo-12-methoxy-4H,10H-(2)-benzopyrano-[4,3-g]-(1)-benzopyran (0.43 millimol) in 2 ml of glacial acetic acid containing 2 ml of hydroiodic acid (57%) was refluxed for 75 minutes. The reaction mixture was then cooled, and the crude product collected as an insoluble solid. One recrystallization from methanol yielded the compound named in the heading (80 mgm; 60% yield) as yellow needles, m.p. 292° C (decomp.).

EXAMPLE 18

2-Carboxy-4-oxo-10,10-dimethyl-12-nitro-4H,10H-(2)-benzopyrano-[4,3-g]-(1)-benzopyran A suspension of 15 gm of 2-acetyl-3-hydroxy-4-nitro-6,6-dimethyl-6H-dibenzo[b,d]pyran (0.048 mol) in 150 ml of ethanol containing 12 gm of diethyl oxalate (0.083 mol) was added all at once to a hot solution of 9.75 gm of sodium (0.424 mol) in 250 ml of ethanol, and the resulting mixture was refluxed for 45 minutes. The reaction mixture was then cooled, concentrated to 50 ml, treated with 100 ml of 2 N hydrochloric acid, and extracted twice with 200 ml of ether. The ether extracts were combined and evaporated to dryness, and the residue was refluxed for 4 hours in 225 ml of a mixture of glacial acetic acid and hydrochloric acid (2:1). The reaction mixture was then poured into ice water, and the crude product collected as the precipitated solid. Recrystallization from glacial acetic acid yielded the compound named in the heading (15 gm; 85% yield) as yellow needles, m.p. 298°–305° C (decomp.).

EXAMPLE 19

2-Carboxy-4-oxo-10,10-dimethyl-12-chloro-4H,10H-(2)-benzopyrano-[4,3-g]-(1)-benzopyran A mixture of 1.13 gm of 2-acetyl-3-hydroxy-4-chloro-6,6-dimethyl-6H-dibenzo[b,d]pyran (3.7 millimols) and 0.95 gm of diethyl oxalate (6.6 millimols) in 20 ml of ethanol was added all at once to a hot solution of 0.76 gm of sodium (33 millimols) in 30 ml of ethanol, and the resulting mixture was refluxed for 2 hours. The reaction mixture was then cooled, concentrated to about 5 ml, diluted with 100 ml of 1 N hydrochloric acid, and extracted twice with 50 ml of chloroform. The combined extracts were evaporated to dryness, and the residue was refluxed for 2 hours in 15 ml of a mixture of glacial acetic acid and hydrochloric acid (2:1). The reaction mixture was then poured into 100 ml of ice water, and the crude product collected as the precipitated solid. Recrystallization from acetic acid yielded the compound named in the heading as a yellow microcrystalline solid (0.78 gm; 56% yield), m.p. 278°–286° C (decomp.).

EXAMPLE 20

2-Carboxy-4-oxo-10,10-dimethyl-12-amino-4H,10H-(2)-benzopyrano-[4,3-g]-(1)-benzopyran A suspension of 6.5 gm of 2-carboxy-4-oxo-10,10-dimethyl-4H,10H-(2)-benzopyrano-[4,3-g]-(1)-benzopyran (0.018 mol) and 29 gm of metallic tin in 100 ml of 2 N hydrochloric acid was refluxed for 30 minutes. The hot reaction solution was decanted from the undissolved tin and cooled, and the precipitated solid was collected and recrystallized from methanol to yield the compound named in the heading as yellow needles, m.p. 273°–278° C (decomp.).

EXAMPLE 21

2-Carboxy-4-oxo-8-amino-10,10-dimethyl-4H,10H-(2)-benzopyrano-[4,3-g]-(1)-benzopyran 22 gm (0.06 mol) of finely powdered 2-carboxy-4-oxo-8-nitro-10,10-dimethyl-4H,10H-(2)-benzopyrano-[4,3-g]-benzopyran (see Example 13) were added over a period of 20 minutes in a nitrogen atmosphere to a suspension of 1 gm of 10% Pd/oval in 1000 ml of water containing 22 gm of sodium borohydride. The resulting mixture was stirred for 25 minutes and then filtered. The aqueous phase was carefully acidified with 2 N hydrochloric acid. The crude product collected as the precipitated solid, and was recrystallized from methanol to yield the compound named in the heading (12 gm; 54% yield), m.p. >340° C (decomp. >200° C).

The compounds of the present invention, that is, those embraced by formula I above and their salts, have useful pharmacodynamic properties. More particularly, they exhibit antiallergic activity in warm-blooded animals, such as rats.

The antiallergic activity of the compounds of the instant invention was ascertained by the so-called PCA-test (passive cutaneous anaphylaxis test) and compared to the antiallergic activity of the known related compound 1,3-bis-(2'-carboxy-chromon-5'-yloxy)-2-hydroxy-propane.

In this test the skin of adult laboratory rats is sensitized by means of intradermal injections of egg albumin-antiserum of exponentially decreasing concentrations, i.e. undiluted, 1:3, 1:9, 1:27, etc. One day later the test animals are administered egg albumin in Evans' Blue solution the size of the blue-colored area of the skin. The test compound is administered i.v. together with the Evans' Blue solution at varying concentrations. Each rat receives 5 mgm of egg albumin dissolved in 1 ml of a 0.25% Evans' Blue solution in a sterile salt solution. 25 to 30 minutes after administration of the dye and the test compound the animals are killed, and the area of blue coloration on the inside surface of the skin is measured in $mm^2$. The PCA-titer is the reciprocal value of that serum dilution at which a blue coloration with a diameter of at least 5 mm is just barely discernable. The reduction in the PCA-titer is a measure of the degree of suppression of allergic reactions, in the present case against albumin, produced by the test compound.

The following table shows the results obtained from this test for a number of compounds of the present invention (A - E) which are representative of the genus embraced by formula I, in comparison with a known, structurally related antiallergic (F), where A = 2-carboxy-4-oxo-10,10-dimethyl-4H,10H-(2)-benzopyrano-[4,3-g]-(1)-benzopyran, B = 2-carboxy-4-oxo-4H,10H-(2)-benzopyrano-[4,3-g]-(1)-benzopyran, C = 2-carboxy-4-oxo-7,8-dimethoxy-10,10-dimethyl-4H,10H-(2)-benzopyrano-[4,3-g]-(1)-benzopyran, D = 2-carboxy-4-oxo-8-hydroxy-10,10-dimethyl-4H,10H-(2)-benzopyrano-[4,3-g]-(1)-benzopyran, E = 2-carboxy-4-oxo-8-(β-hydroxy-ethoxy)-10,10-dimethyl-4-H,10H-(2)-benzopurano-[4,3-g]-(1)-benzopyran, and F = 1,3-bis-(2'-carboxy-chromon-5'-yloxy)-2-hydroxy-propane.

| Compound | % Reduction of PCA-titer | | | | |
|---|---|---|---|---|---|
| | 0.1 mgm | 0.5 mgm | 1.0 mgm (i.v.) | 5.0 mgm | 10.0 mgm |
| A | — | 25 | 71 | — | 90 |
| B | — | — | 64 | — | 86 |
| C | — | — | 67 | — | 83 |
| D | 44 | — | 89 | — | 87 |
| E | 67 | — | 81 | — | 83 |
| F | — | — | 20 | 60 | 89 |

These values clearly show that the compounds embraced by formula I are significantly more effective antiallergics than the known compound.

For pharmaceutical purposes the compounds embraced by formula I or their salts are administered to warm-blooded animals topically, perorally, parenterally or by the respiratory route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, inhalation aerosols, emulsions, syrups, suppositories and the like. One effective parenteral or inhalation dosage unit of the compounds of the formula I or their salts is from 0.083 to 0.84 mgm/kg body weight, and the peroral dosage range is from 0.83 to 8.4 mgm/kg body weight.

The following examples illustrate a few pharmaceutical dosage unit compositions comprising a compound of the formula I or a salt thereof as an active ingredient and represent the best modes contemplated of putting the invention into practical use. The parts are parts by weight unless otherwise specified.

EXAMPLE 22

Tablets

The tablet composition is compounded from the following ingredients:

| | |
|---|---|
| Sodium salt of 2-carboxy-4-oxo-10,10-dimethyl-4H,10H-(2)-benzopyrano-[4,3-g]-(1)-benzopyran | 0.100 parts |
| Stearic acid | 0.010 parts |
| Dextrose | 1.890 parts |
| & Total | 2.000 parts |

Preparation:

The ingredients are admixed in conventional manner, and the mixture is compressed into 2.0 gm-tablets, each of which contains 100 mgm of the benzopyrano-benzopyran salt and is an oral dosage unit composition with effective antiallergic action.

EXAMPLE 23

Ointment

The ointment composition is compounded from the following ingredients:

| | | |
|---|---|---|
| Sodium salt of 2-carboxy-4-oxo-10,10-dimethyl-4H,10H-(2)-benzopyrano-[4,3-g]-(1)-benzopyran | | 2.000 parts |
| Fuming hydrochloric acid | | 0.011 parts |
| Sodium pyrosulfite | | 0.050 parts |
| Mixture (1:1) of cetyl alcohol and stearyl alcohol | | 20.000 parts |
| White vaseline | | 5.000 parts |
| Synthetic bergamot oil | | 0.075 parts |
| Distilled water | q.s.ad | 100.000 parts |

Preparation:

The ingredients are uniformly blended in conventional manner into an ointment, 100 gm of which contain 2.0 gm of the benzopyrano-benzopyran salt. The ointment is an effective antiallergic composition for topical application.

EXAMPLE 24

Inhalation aerosol

The aerosol composition is compounded from the following ingredients:

| | | |
|---|---|---|
| Sodium salt of 2-carboxy-4-oxo-10,10-dimethyl-4H,10H-(2)-benzopyrano-[4,3-g]-(1)-benzopyran | | 1.00 parts |
| Soybean lecithin | | 0.20 parts |
| Propellent gas mixture (frigen 11, 12 and 14) | q.s. ad | 100.00 parts |

Preparation:

The ingredients are compounded in conventional manner, and the composition is filled into aerosol containers with a metering valve which releases 5 to 20 mgm of active ingredient per actuation of the valve. The aerosol spray is a dosage unit composition with effective antiallergic action for administration by the respiratory route.

EXAMPLE 25

Hypodermic solution

The solution is compounded from the following ingredients:

| | | |
|---|---|---|
| Sodium salt of 2-carboxy-4-oxo-10,10-dimethyl-4H,10H-(2)-benzopyrano-[4,3-g]-(1)-benzopyran | | 50.0 parts |
| Sodium pyrosulfite | | 1.0 parts |
| Sodium salt of EDTA | | 0.5 parts |
| Sodium chloride | | 8.5 parts |
| Double-distilled water | q.s.ad | 1000.0 parts |

Preparation:

The individual ingredients are dissolved in a sufficient amount of double-distilled water, the solution is diluted to the indicated concentration with additional double-distilled water, the resulting solution is filtered until free from suspended particles, and the filtrate is filled under aseptic conditions into 1 ml-ampules which are subsequently sterilized and sealed. Each ampule contains 50 mgm of the benzopyrano-benzopyran salt, and the contents thereof are an injectable dosage unit composition with effective antiallergic action.

Analogous results are obtained when any one of the other benzopyrano-benzopyrans embraced by formula I or a salt thereof is substituted for the particular active ingredient in Examples 22 through 25. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition for suppressing reagin-mediated allergic reactions, said composition consisting essentially of an inert pharmaceutical carrier and an effective antiallergic amount of a compound of the formula

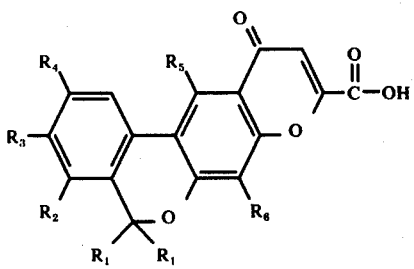

wherein $R_1$ is hydrogen or lower alkyl,
$R_2$, $R_4$ and $R_5$ are each hydrogen, lower alkyl, hydroxyl, lower alkoxy, lower alkanoyloxy, nitro or —$SO_3H$, and
$R_3$ and $R_6$ are each hydrogen, lower alkyl, hydroxyl, lower alkoxy, lower alkanoyloxy, halogen, nitro, —$SO_3H$, hydroxycarbonyl-methoxy, $\beta$-hydroxy-ethoxy or $\beta$-amino-ethoxy,
or a salt thereof.

2. A composition of claim 1, where
$R_1$ is hydrogen, or methyl,
$R_2$ is hydrogen, chlorine or methoxy,
$R_3$ is hydrogen, chlorine, fluorine, hydroxyl, methoxy, acetoxy, nitro or sulfo,
$R_4$ is hydrogen, bromine or methoxy,
$R_5$ is hydrogen, or methyl, and
$R_6$ is hydrogen,
and said salt is an alkali metal salt.

3. A composition of claim 1, where said compound is 2-carboxy-4-oxo-10,10-dimethyl-4H,10H-(2)-benzopyrano-[4,3-g]-(1)-benzopyran or the sodium salt thereof.

4. The composition of claim 1, where said compound is 2-carboxy-4-oxo-10,10-dimethyl-4H,10H-(2)-benzopyrano-[4,3-g]-(1)-benzopyran.

5. The composition of claim 1, where said compound is the sodium salt of 2-carboxy-4-oxo-10,10-dimethyl-4H,10H-(2)-benzopyrano-[4,3-g]-(1)-benzopyran.

6. The method of preventing the symptoms of mediated allergic reactions in a warm-blooded animal in need thereof, which comprises administering to said animal an effective antiallergic amount of a compound of the formula

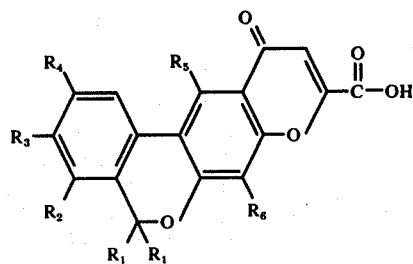

wherein
$R_1$ is hydrogen or lower alkyl,
$R_2$, $R_4$ and $R_5$ are each hydrogen, lower alkyl, hydroxyl, lower alkoxy lower alkanoyloxy, halogen, nitro or —$SO_3H$, and
$R_3$ and $R_6$ are each hydrogen, lower alkyl, hydroxyl, lower alkoxy, lower alkanoyloxy, halogen, nitro, —$SO_3H$, hydroxycarbonyl-methoxy, $\beta$-hydroxy-ethoxy or $\beta$-amino-ethoxy,
or a salt thereof.

7. The method of claim 6, where
$R_1$ is hydrogen, or methyl,
$R_2$ is hydrogen, chlorine or methoxy,
$R_3$ is hydrogen, chlorine, fluorine, hydroxyl, methoxy, acetoxy, nitro or sulfo,
$R_4$ is hydrogen, bromine or methoxy,
$R_5$ is hydrogen, or methyl, and
$R_6$ is hydrogen,
and said salt is an alkali metal salt.

8. The method of claim 6, where said compound is 2-carboxy-4-oxo-10,10-dimethyl-4H,10H-(2)-benzopyrano-[4,3-g]-(1)-benzopyran or the sodium salt thereof.

9. The method of claim 6, where said compound is 2-carboxy-4-oxo-10,10-dimethyl-4H,10H-(2)-benzopyrano-[4,3-g]-(1)-benzopyran.

10. The method of claim 6, where said compound is the sodium salt of 2-carboxy-4-oxo-10,10-dimethyl-4H,10H-(2)-benzopyrano-[4,3-g]-(1)-benzopyran.

* * * * *